US007785585B2

(12) United States Patent
Peele et al.

(10) Patent No.: US 7,785,585 B2
(45) Date of Patent: Aug. 31, 2010

(54) COMPOSITIONS COMPRISING SCLAREOL OR DERIVATIVES THEREOF AND USES THEREOF

(75) Inventors: David Peele, Edenton, NC (US); Dilip Chokshi, Parsippany, NJ (US)

(73) Assignee: Avoca, Inc., Merry Hill, NC (US)

( * ) Notice: Subject to any disclaimer, the term of this patent is extended or adjusted under 35 U.S.C. 154(b) by 92 days.

(21) Appl. No.: 11/803,591

(22) Filed: May 15, 2007

(65) Prior Publication Data

US 2007/0219355 A1 Sep. 20, 2007

Related U.S. Application Data

(62) Division of application No. 11/016,509, filed on Dec. 17, 2004, now Pat. No. 7,588,759.

(51) Int. Cl.
*A61K 35/66* (2006.01)
*A61K 35/74* (2006.01)
*A61K 36/64* (2006.01)
*A61K 36/537* (2006.01)

(52) U.S. Cl. ........................ 424/115; 424/144; 424/746

(58) Field of Classification Search ....................... None
See application file for complete search history.

(56) References Cited

U.S. PATENT DOCUMENTS 3,060,172 A 10/1962 Teague et al.
4,966,783 A * 10/1990 Buckholz et al. ............ 426/565
5,212,078 A * 5/1993 Farbood et al. ............. 435/126
5,804,596 A 9/1998 Majeed et al.
5,906,993 A 5/1999 Braquet et al.
5,945,546 A 8/1999 Subbiah
6,080,401 A * 6/2000 Reddy et al. ............... 424/93.3
6,331,551 B1 12/2001 Subbiah
6,797,287 B2 * 9/2004 Chokshi ........................ 514/8
7,226,625 B2 * 6/2007 Subbiah ...................... 424/746
2005/0008718 A1 1/2005 Subbiah

FOREIGN PATENT DOCUMENTS

EP 1331006 7/2003
WO WO9963978 12/1999
WO WO2005023019 3/2005

OTHER PUBLICATIONS

Peana et al., "Pharmacological Activities and Applications of *Salvia sclarea* and *Salvia desoleana* Essential Oils" 2002, Studies in Natural Product Chemistry, vol. 26, pp. 391-423 XP009117785.
Malone et al., "A pharmacological evaluation of the diterpene (-)-sclareol in intact rats" 1991, Fitoterapia, vol. LXII, No. 2, pp. 123-129 XP009117852.
Ceschel et al., "In vitro permeation through porcine buccal mucosa of *Salvia sclarea* L. essential oil from topical formulations" 1998, Science Techniques et Pratiques STP Pharma Sciences, Paris, Fr, vol. 8, No. 2, pp. 103-106 XP009117864.
Georgieva ZH et al., "Study of the effect of sclareol glycol diterpene on the 3', 5'-AMP level" Database Pubmed [online] 1989, XP002530977.
Anonymous, "Portraits der im Capitulare de Villis aufgelisteten Pflanzen" Internet article [online] 2003, XP002530978.

* cited by examiner

*Primary Examiner*—Vera Afremova
(74) *Attorney, Agent, or Firm*—Hoffmann & Baron, LLP

(57) ABSTRACT

The present invention provides a composition which includes a sclareol or a derivative thereof, wherein the sclareol or a derivative thereof is bound by a glycoprotein matrix. The composition of the invention provides improved potency, stability and bioactivity characteristics of sclareol, or its derivatives.

3 Claims, No Drawings

COMPOSITIONS COMPRISING SCLAREOL OR DERIVATIVES THEREOF AND USES THEREOF

CROSS REFERENCE TO RELATED APPLICATION

This application is a divisional application of U.S. application Ser. No. 11/016,509, filed on Dec. 17, 2004 now U.S. Pat. No. 7,588,759.

BACKGROUND OF THE INVENTION

The present invention relates to compositions containing sclareol or a derivative thereof and methods for increasing cyclic adenosine monophosphate activity.

It has been reported that approximately 40% of the United States population suffer from obesity (Glazer, *Arch. Intern. Med.* 2001, 161:1814-1824). Obesity has been associated with many illnesses, such as cardiovascular disease, respiratory illnesses, sleep apnea, Pick-Wichian syndrome, diabetes mellitus and pulmonary hypertension In order for any weight loss regime to be effective, the ability to burn fat must be increased so that consumed and stored fat is utilized. In addition to weight loss, an increased ability to burn fat is also important for, for example, body builders, athletes, etc. and individuals who desires to maintain a lean body mass.

Cyclic adenosine monophosphate (cAMP) is an important second messenger that carries signals from the cell surface to proteins within a cell. It is believed that cAMP exerts its effect by activating various protein kinases within cells. Elevated levels of intracellular cAMP have been reported to be involved in numerous metabolic processes.

For example, it has been reported that elevated levels of cAMP enhance the degradation of glycogen, and also play a role in inhibiting the synthesis of glycogen, the major storage form of glucose. In addition, in adipocytes (i.e., fat-storage cells) an increase in cAMP levels activates a cAMP dependent protein kinase, which in turn, activates the enzyme lipase. Lipase is responsible for the hydrolysis of triacylglycerols to fatty acids, also known as lipolysis. Furthermore, elevated cAMP levels have been reported to increase synthesis of hormones, such as estrogen, progesterone, and testosterone.

Therefore, compositions which can increase intracellular levels of cAMP would be beneficial in, for example, inducing weight loss, increasing lipolysis and/or increasing libido.

It is reported that sclareolide, a derivative of sclareol, is effective in increasing cyclic AMP activity. Currently, there are several products containing sclareolide. These products include, for example, Xenadrine 40+ available from Cytodyne LLC. and HOT-ROX™.

Unfortunately, the currently available products containing sclareolide do not provide much, if any benefit. One reason being that the amount and quality (e.g. potency, stability and bioactivity) of the sclareolide present in the currently available products is inadequate.

Sclareol is typically obtained from the clary sage plant (*Salvia sclarea*). However, there is limited availability of clary sage. Accordingly, the availability of sclareol and its derivatives (e.g., sclareolide) are also limited.

Therefore, there is a need for novel compositions of sclareol or derivatives thereof having greater potency, increased stability and bioactivity. Thus, fewer amounts of sclareol or its derivatives are needed to achieve beneficial effects, such as those described above.

SUMMARY OF THE INVENTION

The present invention is for a composition comprising sclareol or a derivative thereof, where the sclareol or derivative thereof is bound by a glycoprotein matrix. In one embodiment, the derivative is sclareolide. In another embodiment, the composition also comprises microorganisms. In yet another embodiment, the microorganisms produce the glycoprotein matrix.

In a preferred embodiment, the microorganisms include yeast, such as *Saccharomyces cervisiae*. In another embodiment, the microorganisms include bacteria such as *Lactobacillus*, including *Lactobacillus acidophilus, Bacterium bifidus* or a combination thereof. In yet another embodiment, the microorganisms include both yeast and bacteria.

In one aspect of the invention, the composition also comprises stabilizers and/or additives.

The present invention is also directed to a nutritional supplement comprising sclareol or a derivative thereof, where the sclareol or derivative is bound by a glycoprotein matrix.

In another aspect of the invention, the present invention is also directed to a method for increasing cyclic adenosine monophosphate activity in a host. The method comprises administering to a host, an effective amount of a composition comprising sclareol or a derivative thereof, where the sclareol or derivative is bound by a glycoprotein matrix.

In another aspect of the invention, a method for inducing weight loss in a host in need thereof is provided. The method comprises administering to a host, an effective amount of a composition comprising sclareol or a derivative thereof, where the sclareol or derivative is bound by a glycoprotein matrix.

In yet another aspect of the invention, a method for increasing libido in a host in need thereof is provided. The method comprises administering to a host, an effective amount of a composition comprising sclareol or a derivative thereof, where the sclareol or derivative is bound by a glycoprotein matrix.

In yet a further aspect of the invention, a method for increasing lipolysis in a host in need thereof is provided. The method comprises administering to a host, an effective amount of a composition comprising sclareol or a derivative thereof, where the sclareol or derivative is bound by a glycoprotein matrix.

DETAILED DESCRIPTION OF THE INVENTION

In accordance with the present invention, a composition is provided which includes a sclareol or a derivative thereof, wherein the sclareol or a derivative thereof is bound by a glycoprotein matrix. The composition of the invention provides improved potency, stability and bioactivity characteristics of sclareol, or its derivatives.

Sclareol

Sclareol is a bioactive diterpene having the general formula shown in formula I below:

Formula I

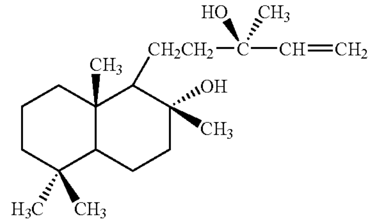

Sclareol is typically obtained from the clary sage plant (*Salvia sclarea L.*). Usually, sclareol is obtained from the flower heads of a clary sage plant. However, the claimed invention is not limited to sclareol derived from clary sage. Any botanical organism known in the art as containing sclareol can be used for obtaining sclareol.

Sclareol can be obtained from an organism by any method known to those in the art. Typically, sclareol is obtained by solvent extraction. For example, U.S. Pat. No. 3,060,172 describes a process for the isolation of sclareol from clary sage. See also, U.S. Pat. No. 5,945,546. U.S. Pat. Nos. 3,060,172 and 5,945,546 are hereby incorporated by reference.

The solvent for extracting sclareol can be any solvent, such as a polar solvent. An example of a polar solvent is water.

The term "sclareol" as used herein in this specification refers to sclareol and derivatives of sclareol. An example of a sclareol derivative is sclareolide. Sclareolide has the general formula shown below in formula II:

Formula II

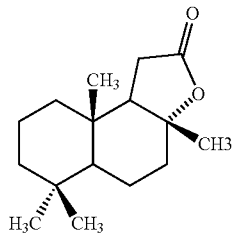

Sclareolide can be prepared by any method known to those in the art. For example, sclareolide is typically prepared by either chemical oxidation followed by lactonization of sclareol or by biotransformation of sclareol using a yeast strain. Exemplary methods of producing sclareolide include those methods disclosed in U.S. Pat. No. 5,525,728 to Schneider et al., U.S. Pat. No. 5,247,100 to Gerke et al., and German Patent Application DE 3942358 to Gerke et al.

Briefly, these processes use a ruthenium catalyst and an oxidation step to convert sclareol into a crude sclareolide product. Other exemplary methods of converting sclareol to sclareolide that are more commonly used include the biotransformation and fermentation methods described in U.S. Pat. Nos. 4,970,163 and 5,212,078, both to Farbood et al. Sclareolide produced by these described methods is normally provided in wet or dry cake form, and is generally from about 90% to 98% pure. The disclosures of these patents setting forth methods of producing sclareolide from sclareol are incorporated herein by reference in their entirety.

Glycoprotein Matrix

The sclareol is bound by a glycoprotein matrix. A glycoprotein matrix is a molecular network comprised of a plurality of glycoprotein molecules bound together. Glycoproteins are composed of carbohydrate groups and simple proteins.

The carbohydrate in the glycoprotein can be any suitable carbohydrate, such as a monosaccharide, disaccharide, oligosaccharide, or polysaccharide. Oligosaccharide is preferred. The protein of the glycoprotein can be any suitable polypeptide. The ratio of carbohydrate to protein in the glycoprotein matrix can vary, for example, from 99:1 to 1:99 by weight. A ratio of approximately 1:1 is preferred.

Composition

The composition of the present invention comprises a glycoprotein matrix bound to at least one sclareol. The glycoprotein matrix and sclareol can be associated with each other physically and/or chemically, such as by chemical reaction, and/or secondary chemical bonding, e.g., Van der Waals forces, etc. Not being bound by theory, it is believed that the glycoprotein matrix may be bound to the sclareol by weak covalent bonds.

The composition can contain essentially any percentage of sclareol as desired. For example, the percentage of sclareol can vary between 0.1 and 99% by weight of the composition depending upon the sclareol and the desired result in the host. In a preferred embodiment, the composition will contain between about 5 and 50% by weight of the composition.

The ratio of glycoprotein matrix to sclareol can also vary. It is preferred that the ratio of glycoprotein matrix to sclareol will be such that all or nearly all of the sclareol in the composition is bound by glycoprotein matrix. To ensure that essentially all of the sclareol is bound, higher ratios of glycoprotein matrix to sclareol can be used.

The invention also contemplates a composition where there may be insufficient glycoprotein to bind the entire amount of the sclareol. In such cases, the ratio of glycoprotein matrix to sclareol can be less.

In a preferred embodiment, the source of the glycoprotein matrix is microorganisms and, therefore, a preferred composition of the invention will include microorganisms. At the end of the manufacturing process of the composition, these microorganisms are usually inactive.

The glycoprotein matrix can be bound to the sclareol by allowing the microorganisms to ferment, in the presence of the sclareol. As used herein, fermentation is the process by which microorganisms metabolize raw materials, such as amino acids and carbohydrates, to produce glycoproteins.

The microorganisms produce glycoproteins both intracellularly and extracellularly The intracellular glycoproteins will mainly be located in the cytoplasm of the microorganism or become part of the microorganism's physical structure. The glycoproteins from the microorganism that forms the glycoprotein matrix is mainly extracellular and, therefore, is available to be bound to the sclareol. Intracellular glycoproteins can also be made accessible for binding to the sclareol by rupture of the microorganisms after glycoprotein production.

Microorganisms that produce a glycoprotein matrix include, but are not limited to, yeast and some bacteria. A preferred yeast is *Saccharomyces cervisiae*. Bacteria that produce glycoprotein include bacteria within the genus *Lactobacillus*. For example, such bacteria include, but are not limited to, *Lactobacillus acidophillus, Lactobacillus bulgaricus, Lactobacillus caucasicus*, and *Bacterium bifidus*. Preferred bacteria include *Lactobacillus acidophilus* or *Bacterium bifidus*.

Combinations of microorganisms can be used provided that at least one of the microorganisms produces glycoprotein. When using combinations of microorganisms, the growth of one type of microorganism should not prevent the growth of the other. For example, various types of different yeast that produce glycoprotein can be used. Also, yeast and bacteria can be combined to produce glycoprotein. This combination is particularly advantageous because various types of bacteria, such as *Lactobacillus acidophillus*, also produce glycoproteins. For example, in one embodiment, the microorganism includes a combination of *Lactobacillus acidophilus* and *Bacterium bifidus.*

Methods for binding compounds with a glycoprotein matrix are disclosed in U.S. application Ser. Nos. 09/757,222 and 09/962,917, both assigned to PharmaChem Labs. The methods disclosed in these above-referenced applications can be modified for binding a glycoprotein matrix to sclareol. The methods disclosed in U.S. application Ser. Nos. 09/757,222 and 09/962,917 are hereby incorporated by reference.

Stabilizers and Additives

The composition of the invention can also include stabilizers and/or additives. Stabilizers and additives can include, for example, pharmaceutically acceptable buffers, excipients, diluents, surfactants, adjuvants, flavorings, and the like. The amounts of such additives can be determined by one skilled in the art.

The additive can be any additive known to those skilled in the art. Additives can be added which, for example, improve the viability of the microorganisms that produce the glycoprotein or increase the yield of glycoprotein that becomes bound to the active ingredient. For example, salts can be added in order to increase the viability of the microorganism. Such salts include, but are not limited to, calcium carbonate, ammonium sulfate, and magnesium sulfate. Calcium carbonate is preferred. The amount of salt added to the microorganism solution should be sufficient to obtain the desired result of improving the viability of the organism, as is known in the art. A preferred range of salt added to the microorganism solution is between about 25 to about 150 grams of salt per 375 grams of microorganism, such as *Saccharomyces Cervisiae*. Approximately 40 g of salt per 375 gram of microorganism is most preferred.

The composition of the invention can be manufactured so as to be biocompatible. Since the sclareol composition is to be ingested, the microorganism used to produce the glycoprotein matrix should be suitable for consumption by mammals, especially humans. Examples of such microorganisms include *Lactobacillus acidophillus* and *Saccharomyces cervisiae.*

Dosage and Administration

The glycoprotein matrix compositions containing sclareol can be administered topically or systemically. Systemic administration can be enteral or parenteral. Enteral administration is preferred. For example, the compositions can easily be administered orally. Liquid or solid (e.g., tablets, gelatin capsules) formulations can be employed. The formulation can include pharmaceutically acceptable excipients, adjuvants, diluents, or carriers. The composition can also be administered intravenously, with a suitable pharmaceutical carrier (vehicle) or excipient, as understood by those skilled in the art.

In a preferred embodiment, the compositions of the claimed invention are formulated in the form of a nutritional supplement. The nutritional supplement is typically administered orally. The supplement can be a liquid or solid (e.g., tablets, gelatin capsules) formulation.

An effective amount of a claimed composition is an amount which is effective in increasing cyclic adenosine monophosphate activity. The increase in cyclic adenosine monophosphate activity results in, for example, inducing weight loss, increasing libido, and/or increasing lipolysis. An effective amount is determined by methods familiar to clinicians and physicians during pre-clinical and clinical trials.

Typically, the dose for sclareolide is approximately 30 to 75 mg/dose. In general, the dose for sclareolide bound by a glycoprotein matrix will be less than that of just sclareolide alone. Therefore, a suitable dose of sclareolide bound by a glycoprotein matrix is approximately 5 to 50 mg/dose.

Host

In a preferred embodiment the host is a mammal. Mammals include, for example, humans, as well as pet animals such as dogs and cats, laboratory animals such as rats and mice, and farm animals such as horses and cows. Humans are most preferred.

A host in need of increasing cyclic adenosine monophosphate (cAMP) is, for example, any host with a condition in which an increase in cAMP activity is beneficial to the health or well-being of the host. Examples of conditions in which a host would benefit from an increase in cAMP activity include, but are not limited to, a host in need of weight loss, a host in need of increasing lipolysis, a host in need of increasing libido, and a host in need of inhibiting adipogenesis.

A host in need of weight loss is, for example, any host where the weight of the host is not beneficial for its health. Another example of a host in need of weight loss is, for example, a host that is unhappy with it's appearance due to excess weight. Some examples of hosts in need of weight loss include, but are not limited to, hosts that suffer from diabetes mellitus and overweight individuals.

A host is considered overweight when the body weight of the mammal is greater than the ideal body weight according to the height and body frame of the host. The ideal body weight of a host is known to those skilled in the art. A host is considered in need of weight loss if its body weight is at least about 10%, preferably at least about 30%, more preferably at least about 60%, and most preferably at least about 100% greater than their ideal body weight.

A host, for example, a human, is considered obese when its body weight is increased beyond the limitation of skeletal and physical requirement as the result of excessive accumulation of fat in the body. Obesity can be the result of many different forces, such as, for example, overeating or a medical condition. A medical condition that could result in obesity is, for example, a low metabolic rate.

Morbid obesity occurs when an individuals weight is two, three or four times the ideal weight for that individual, and is so-called because it is associated with many seriously life-threatening disorders.

A host in need of increasing lipolysis is, for example, any host that desires to hydrolyze lipids, e g., a host that desires to burn stored body fat. Other examples of a host in need of increasing lipolysis is, for instance, a host having an amount of body fat that is not optimal for the health of the host or a host that desires to increase its lean body mass. Some examples of hosts in need of increasing lipolysis include, but are not limited to, hosts that are overweight or athletes, such as bodybuilders.

An amount of body fat that is considered not to be optimal is when the amount of body fat of the host is greater than the ideal body fat according to the height and body frame of the host. The body fat of a host, for example, a human, is considered not to be optimal when its body fat is increased beyond the limitation of skeletal and physical requirement as the result of excessive accumulation of fat in the body.

The ideal body fat of a host is known to those skilled in the art. A host is considered in need of lipolysis if its body fat is at least about 10%, preferably at least about 30%, more preferably at least about 60%, and most preferably at least about 100% greater than their ideal amount of body fat. For example, in humans, optimal body fat amount are about 15% to about 19% for 20-29 year old males and about 19% to about 23% for 20-29 year old females.

A host in need of inhibiting adipogenesis is, for example, any host that desires to inhibit the production or deposition of fat. The production of fat includes, for instance, the conversion of carbohydrates or proteins to fat. Other examples of a host in need of inhibiting adipogenesis is, for example, a host having an amount of body fat that is not optimal for the health of the host. Some examples of hosts in need of inhibiting adipogenesis include, but are not limited to, hosts that are overweight or athletes.

A host in need of increasing libido is, for example, any host having a suppressed or decreased libido. Another example of a host in need of increasing libido is, for instance, where the libido level is not beneficial for the mental well-being of the host or a host that desires to increase their libido. Some examples of host in need of increasing libido include, but are not limited to, hosts on mediations, such as anti-depressants, which decreases or suppresses libido, and hosts with low levels of hormones.

EXAMPLES

Example 1

Preparation of Selareol or Sclareolide Bound to Glycoprotein Matrix

The method employs preparing, in a first container, an aqueous solution of sclareol or sclareolide. In a second container, an active yeast solution is prepared. Active baker's yeast, *Saccharomyces cervisiae*, is added to water to form an aqueous solution. Maltose and gum acacia are then added.

The first container containing the sclareol or sclareolide is then inoculated very slowly into the active yeast solution to form a live fermented solution. The mixture is allowed to ferment for four to six hours. To promote yeast growth, plant proteins and carbohydrates are added. Proteolytic enzyme, such as papain, is then added.

*Lactobacillus acidophilus* is added to the live fermented solution and allowed to ferment for about 2 hours. Active fermentation is then stopped by heating the solution to 160-170° F. for three hours.

The fermented mineral solution is then homogenized in a shearing pump (Charles Ross & Sons Corp.) for approximately 1-2 hours and spray dried (NIRO, Nicholas Engineers Research Corp.) for approximately 4 hours. The resulting product is a powder containing the sclareol-glycoprotein matrix complex or sclareolide-glycoprotein matrix complex.

Example 2

Effect of Sclareolide+GPM on Lipolysis

Human subcutaneous preadipocytes were obtained from human patients undergoing liposuction and pooled. The characteristics of the patients are shown below:

Sex: F

B.M.I.: 27.25 (avg.)

AGE: 43 (avg.)

The human subcutaneous preadiposytes were designated lot #SL0028.

Preadipocytes were plated in 96-well plates and allowed to differentiate in the absence of compounds (e.g., sclareolide or sclareolide+GPM) for about two weeks. On the day of the assay, the culture medium was removed and the cells were washed gently with Krebs-Ringer buffer (KRB) in the following manner. 120 μl of medium in the wells was removed and 200 μl/well of KRB was added. The KRB in the wells was removed and another aliquot of 200 μl/well of the KRB was added. The wells were washed one row at a time to ensure that the cells remained moist and stayed attached to the plate.

Next, all of the KRB was removed and the cells were treated with 150 μl/well of the controls or 150 μl/well of the test compounds (resuspended in KRB with 1% BSA), either 1) sclareolide at 10 μl/ml or 2) sclareolide plus GPM at 7.5 μl/ml, and incubated at 37° C. for five hours. The assay was performed in triplicate.

At the end of the treatment, 100 μl/well of the conditioned media was removed from the assay plate and added to the corresponding well of a new plate. To the new plate, 100 μl/well of glycerol assay reagent was added. The new plate was then incubated at 25° C. for 15 minutes.

The optical density of each well of the new plate was measured at 540 nm. The optical density is shown below:

| | Sclareolide Concentration | % Increase in Lipolysis over Control |
|---|---|---|
| Sclareolide | 10 μg/ml | 55% |
| Sclareolide + GPM | 7.5 μg/ml | 137% |

As shown in the above table, sclareolide and sclareolide+GPM significantly increased lipolysis over the control.

Surprisingly, the lipolysis observed from sclareolide+GPM (which contains a lower concentration of sclareolide) was substantially greater than that of sclareolide alone.

What is claimed is:

1. A nutritional composition comprising an effective amount of a glycoprotein matrix bound sclareol or sclareolide, wherein said glycoprotein matrix bound sclareol or sclareolide is obtained by fermenting *Saccharomyces cerevisiae* and bacteria in the presence of sclareol or sclareolide, and subsequently isolating the glycoprotein matrix bound sclareol or sclareolide from the fermentation medium, wherein the bacteria is from genus *Lactobacillus*, and wherein the sclareol or sclareolide is obtained from *Salvia sclarea L.*

2. The nutritional composition according to claim 1, wherein the glycoprotein matrix bound sclareol or sclareolide is present in an amount of approximately 5 to 50 mg/dose.

3. The nutritional composition according to claim 1, wherein the bacteria is *Lactobacillus acidophillus, Lactobacillus bulgaricus*, or *Lactobacillus caucasicus.*

* * * * *